United States Patent [19]

Griffin

[11] Patent Number: 4,931,395
[45] Date of Patent: Jun. 5, 1990

[54] MONOCLONAL ANTIBODY SPECIFIC TO NEUTROPHILS

[75] Inventor: James D. Griffin, Sherborn, Mass.

[73] Assignee: Dana-Farber Cancer Institute, Boston, Mass.

[21] Appl. No.: 70,202

[22] Filed: Jul. 6, 1987

Related U.S. Application Data

[63] Continuation-in-part of Ser. No. 938,864, Dec. 8, 1986, abandoned.

[51] Int. Cl.$^5$ .................. C12N 5/00; C07K 15/00; C07K 15/04
[52] U.S. Cl. .................. 435/240.27; 435/172.2; 435/70.21; 530/387; 530/809; 935/104; 935/108; 935/110
[58] Field of Search .................. 530/387, 388, 809; 435/68, 70, 172.2, 240.27, 948; 935/100, 102–104, 110; 436/548

[56] References Cited

PUBLICATIONS

P.A.T. Tetteroo et al., Neutrophil Activation Detected by Monoclonal Antibodies, J. Immuno. 136(9):3427–3432 (May, 1986).
Laskin, D. L. et al, "Stimulation of Human Neutrophilic Granulocyte Chemotaxis by Monoclonal Antibodies", J. Immunol. 134(2):1146–1152, Feb. 1985.
Melnick, D. A. et al., "Activation of Human Neutrophils by Monoclonal Antibody PMN7C3: Cell Movement and Adhesion Can Be Triggered Independently from the Respiratory Burst", Blood 67(5):1388–1394, May 1986.

Primary Examiner—Margaret Moskowitz
Assistant Examiner—Kay E. Cheney
Attorney, Agent, or Firm—Myron C. Cass

[57] ABSTRACT

A hybrid cell line capable of producing monoclonal antibodies uniquely specific to human neutrophils. The monoclonal antibody has no reactivity with other human peripheral blood cells and virtually no reactivity with granulocyte precursors or other cells in bone marrow. Further, there is no reactivity with human acute leukemia cells. One of the partners in the hybridoma fusion of a mouse spleen cell developed from using highly purified human granulocytes as the immunization agent. The monoclonal antibody further is characterized by its capability of being used to enumerate and isolate neutrophils in normal peripheral blood and patients with acute leukemia.

10 Claims, No Drawings

MONOCLONAL ANTIBODY SPECIFIC TO NEUTROPHILS

This invention was made with Government support under PHS Grant #CA 36167.

CROSS REFERENCE TO RELATED APPLICATION

This is a continuation-in-part application of pending application Ser. No. 938,864, filed Dec. 8, 1986, of the same title now abandoned.

This invention relates to a hybridoma cell line which produces a monoclonal antibody which binds to the neutrophil population of white blood cells. The invention thereby enables direct immunoassay of neutrophils in peripheral blood of humans by the specific binding capability of this monoclonal antibody, and further enables selective depletion of neutrophils from a peripheral blood sample.

BACKGROUND OF THE INVENTION

Peripheral blood in the circulatory system of a human is comprised principally of red blood cells, erythrocytes, and white blood cells, leukocytes. The function is leukocytes and their clinical relevance has generated great interest in the scientific community. The family of white blood cells is comprised of neutrophils, monocytes, eosinophils, basophils and lymphocytes, which have numerous subsets.

Neutrophils, monocytes, eosinophils and basophils are known as phagocytes because their primary function in the human immune system is to phagocytose or ingest bacteria and other microorganisms. These cells are produced in the bone marrow of a human. However, each of these phagocytes has different functions and behaves as a related but separate system. Although originating in bone marrow, phagocytic cells do enter into and circulate in peripheral blood.

The general function of the phagocyte system is to achieve phagocytosis of substances recognized as foreign and to assist in the development of an immune response against a foreign substance. Neutrophils are very efficient as a phagocyte for bacteria that have been coated with an antibody and not so efficient for bacteria without antibody coating. The major function of the neutrophil is to prevent invasion by pathogenic microorganisms by localizing and killing them after their invasion. In order to successfully attack an invading microorganism, the neutrophil will exit the peripheral blood, migrate to the tissue area of the infection's start and then, recognize, kill and digest the microorganism.

The neutrophil is the most common cell in bone marrow and the most common leukocyte in peripheral blood. One microliter of a normal whole blood sample includes, on average, $5 \times 10^3$ leukocytes of which 3,075 are neutrophils, 150 are eosinophils, 25 are basophils, 250 are monocytes and 1500 are lymphocytes. The departure from the normal concentration of neutrophils in peripheral blood has recognized clinical relevance. Thus increased concentrations sometimes termed "neutrophilia", may evidence certain disease or physical conditions while decreased concentrations of neutrophils in peripheral blood, sometimes termed "neutropenia" would have different clinical relevance. For instance, an absolute neutrophil count of less than 500 cells per microliter is a life-threatening condition since a patient with such an abnormal count is highly susceptible to life threatening bacterial or fungus infections. Neutropenia may result from cytotoxic drugs, such as administered in treatment of cancer or leukemia. There are numerous congenital and acquired diseases associated with abnormalities of neutrophil function, as well. Assay of neutrophils in peripheral blood is an important part of a total leukocyte count.

This invention provides a novel monoclonal antibody to an antigenic site on the surface of a neutrophil. Such a monoclonal antibody can perform a variety of different functions depending on how it is used, i.e., how labelled, such as with fluorescein or Biotin, for instance, or conjugated to a bead or microsphere, magnetic or non-magnetic, for instance, for identification and enumeration of human neutrophils. The advantages to be derived from such a specific monoclonal antibody clearly are desirable.

SUMMARY OF INVENTION

A cell line which produces a monoclonal antibody specific to a surface protein antigen expressed by neutrophils circulating in peripheral blood of a human. Attendant advantages from assay applications of such a specific antibody are realized.

The monoclonal antibody demonstrates no reactivity with other human peripheral blood cells, and virtually no reactivity with granulocyte precursors or other cells in bone marrow. The monoclonal antibody is produced by a hybridoma cell line where one of the partners to the fusion was derived from immunization using purified human granulocytes.

PREFERRED EMBODIMENT OF THE INVENTION

The monoclonal antibody of the invention is identified by the designation 1D3. It was developed from the fusion of mouse spleen cells immunized with purified human granulocytes and mouse myeloma cells by standard procedure described by Kohler and Milstein [Nature, 256, 495–497 (1975)].

The human granulocytes used in the immunization procedure were specifically prepared. Blood was obtained by venipuncture from humans and mononuclear cells were separated from granulocytes and red blood cells by Ficoll-Hypaque gradient density sedimentation, 1.077 g/cc. Red blood cells and granulocytes then were separated by diluting the red cell/granulocyte pellet with Hanks balanced salt solution and adding 1/10 volume of 4% high molecular weight Dextran. The granulocytes were collected and any residual erythrocytes were lysed with hypotonic buffer. For immunization, the granulocytes were suspended in phosphate buffered saline (PBS).

$10^6$ of these highly purified human granulocytes were injected into the spleen of an anesthetized Balb C mouse. Ten days following intrasplenic immunization, the mouse was boosted with $10 \times 10^6$ similarly purified granulocytes injected intravenously into a tail vein of the mouse. Three days later, the spleen of the mouse was recovered and the spleen cells harvested by conventional techniques.

The fusion to form hybridomas followed. The spleen cells were washed and mixed with the NS-1 plasmacytoma cell line at a ratio of 8 spleen cells to 1 NS-1 cell in serum free medium. The cells were centrifuged to pellet form and suspended in 0.5 ml of 30% polyethylene glycol for eight minutes at 25° C. Then, the polyethylene glycol was decanted, the cells diluted in HAT media and distributed to microliter plates.

Tests for reactivity of the monoclonal antibody 1D3 were performed by indirect immunofluorescense and flow cytometric procedure, screening being for reactivity with purified human granulocytes. The 1D3 monoclonal antibody was selected in an effort to identify an antibody which was absolutely selective for granulocytes and further, was characterized by very high antigen density. The 1D3 monoclonal antibody reacted with more than 90% of granulocytes derived from twenty five of twenty five blood donors tested. 1D3 did not react with purified monocytes, T cells (E+cells), B cells/NK cells (E−cells); it further reacted with only 3% of normal bone marrow mononuclear cells. The 1D3 did not react with eosinophils or basophils so that it is truly neutrophil specific.

Further reactivity testing with the 1D3 monoclonal antibody demonstrated no reaction with tonsil cells or phytohemagglutinin-activated peripheral blood T cells. The antibody was tested for reactivity with several human cell lines. The HL 60 cell line was found to be weakly reactive, i.e., about 26%. The U937, KG1, K562 and Daudi cell lines were found to be unreactive with 1D3. The 1D3 antibody demonstrated no reactivity with 6 samples of human acute lymphoblastic leukemia cells and 5 samples of human acute myeloblastic leukemia cells.

The 1D3 monoclonal antibody is unique because of its exceptional specificity for human neutrophils. The antibody has no reactivity with other human peripheral blood cells and virtually no reactivity with granulocyte precursors or other cells in bone marrow. Since the antibody is highly specific for neutrophils and is present in such high antigen density, detection of granulocytes by any method such as immunofluorescense or immunohistochemistry is greatly facilitated. This monoclonal antibody would be useful for identification and enumeration of human neutrophils. The lack of reactivity of 1D3 with human leukemic cells is of potential clinical relevance. Virtually all previously reported monoclonal antibodies reactive with neutrophils also react with some acute myeloblastic leukemia cells. Thus, 1D3 antibody will provide a capability of enumerating neutrophils correctly in the setting of acute leukemia.

A sample of the hybrid cell capable of producing 1D3 monoclonal antibodies is on deposit with the American Type Culture Collection (A.T.C.C.) 12301 Parklawn Drive, Rockville Md. 20852 and is assigned No. HB 9445.

Attempts to biochemically characterize the antigen identified by the 1D3 monoclonal antibody have encountered unusual difficulties. Three different methods were performed as follows: (1) Wester Blots of lysed and extracted neutrophils; (2) Affinity column purification of the 1D3 antigeon from neutrophils; (3) Iodination of the neutrophils before extraction and then, affinity column purification of the antigen from the neutrophils. The same standard laboratory procedure listed used to isolate cells for immunization in producing hybridoma was used to isolate neutrophils from whole blood. The molecular weight of the 1D3 antigen was not determined by these methods at the time.

Attempts to cellularly characterize the cell surface receptor or antigen recognized by the 1D3 monoclonal antibody were made by their selective removal from peripheral blood cell samples. Two procedures were employed for this purpose, as follows:

I. Flow cytometric and cell sorting techniques were employed using an EPICS® instrument marketed by Coulter Corporation of Hialeah, Fla. Those leukocytes demonstrating fluorescent positivity following a reaction with the 1D3 monoclonal antibody and GAM-FITC fluorescent label were removed by cell sorting technique. The sorted cells were stained with Wright's stain and classified morphologically. A minimum of 500 leukocytes cells were counted in each sample tested.

A total of twenty normal adult peripheral blood samples were evaluated in this manner. In these samples, at least 92% of mature segmented neutrophils marked positive with the 1D3 antibody.

II. In this procedure, cell separation by means of magnetic microspheres conjugated to the 1D3 antibody was conducted. Normal adult peripheral blood samples were treated by lysing or other technique to remove red blood cells without adversely affecting residual leukocytes. The leukocytes were then analyzed cytomorphologically after being stained with Wright's stain. Using the 1D3 conjugated magnetic microspheres introduced to a sample, the leukocytes having neutrophils bound thereto were withdrawn from the sample. The residual negative cells were then evaluated morphologically for the presence of neutrophils.

Nine (9) peripheral blood samples were tested in this manner. Less than 0.2% neutrophils were observed in these residual cell samples, on the average. Again, a minimum of 500 leukocyte cells were counted.

The data obtained from these tests established that the population of white blood cells to which the 1D3 antibody binds specifically was the neutrophil population.

The cellular character of the cell surface receptor or antigen recognized by the 1D3 monoclonal antibody has been defined under reducing and non-reducing conditions. Under reducing conditions, the 1D3 antigen has a molecular weight of 48,000 daltons. Under non-reducing conditions, the 1D3 antigen was identified as having a broad band with a molecular weight range of 48,000 to 60,000 daltons. The 1D3 antigen was isolated from circulating granulocytes obtained from heparinized peripheral human blood by density gradient centrifugation and identified as having a single form.

The equivalent of $4 \times 10^7$ cells were tested on SDS-polyacrylamide electrophoresis (5–15% gradient) carried out on a discontinuous vertical slab gel. A modified procedure of that described in a publication by U. K. Laemole, in Nature 227,680 (1980) was employed. After electrophoresis, the proteins in the acrylamide slab were electroblotted to a sheet of nitrocellulose. The molecular weight markers of the nitrocellulose paper were stained for protein with amino black B. The remainder of the nitrocellulose paper was blocked with a buffer containing non-fat dry milk for immunodetection with anti-1D3 conjugated to the radioactive marker, Iodine 125 ($^{125}I$). The anti-1D3-$^{125}I$ was then reacted with the nitrocellulose, binding to the 1D3 antigen. After washing away the unbound radio-iodinated antibody, the immunoblot was visualized by autoradiography using Kodak XAR film. Upon development of the Kodak XAR film, bands appeared where the 1D3 antigen had migrated. In this manner, the 1D3 antigen to which the 1D3 monoclonal antibody binds so specifically could be characterized.

I claim:

1. A cell line produced by a hydridoma technique which produces a monoclonal antibody having all of the identifying characteristics of the 1D3 monoclonal antibody which specifically binds to the 1D3 antigen of neutrophils and which does not significantly bind to other human peripheral blood cells and which does not significantly bind to granulocyte precursors in bone marrow, said 1D3 antigen having a molecular weight of approximately 48,000 daltons defined under reducing conditions and a molecular weight in the approximate range of 48,000-60,000 daltons defined under non-reducing conditions.

2. The cell line of claim 1 wherein said monoclonal antibody does not significantly bind to human acute lymphoblastic leukemia cells.

3. The cell line of claim 1 wherein said monoclonal antibody does not significantly bind to human acute myeloblastic leukemia cells.

4. The cell line of claim 1 wherein said monoclonal antibody does not significantly bind to human acute leukemia cells.

5. A cell line produced by a hybridoma technique having all the identifying characteristics of the sample on deposit with the American Type Culture Collection Deposit No. HB 9445.

6. A monoclonal antibody which specifically binds to an antigen on the surface of a neutrophil, said antigen having a molecular weight of approximately 48,000 daltons defined under reducing conditions and a molecular weight in the approximate range of 48,000-60,000 daltons defined under non-reducing conditions, said monoclonal antibody having all of the identifying characteristics of the 1D3 monoclonal antibody and further characterized as not significantly binding to:
   A. human acute leukemia cells,
   B. human peripheral blood cells other than neutrophils, and
   C. granulocyte precursors in bone marrow.

7. The monoclonal antibody of claim 6 produced by the hybrid cell line having all the identifying characteristics of the A.T.C.C. deposit No. HB 9445.

8. The monoclonal antibody of claim 6 in which said human acute leukemia cells comprise acute lymphoblastic leukemia cells.

9. The monoclonal antibody of claim 6 in which said human acute leukemia cells comprise acute myeloblastic leukemia cells.

10. The monoclonal antibody identified as 1D3 produced by the hybridoma cell line sample on deposit with the A.T.C.C. and assigned No. HB 9445.

* * * * *